(12) United States Patent
Yoon

(10) Patent No.: US 9,901,401 B2
(45) Date of Patent: Feb. 27, 2018

(54) INTELLIGENT SURGERY SYSTEM

(71) Applicant: Sang Jin Yoon, Seoul (KR)

(72) Inventor: Sang Jin Yoon, Seoul (KR)

(*) Notice: Subject to any disclaimer, the term of this patent is extended or adjusted under 35 U.S.C. 154(b) by 463 days.

(21) Appl. No.: 14/347,532

(22) PCT Filed: Sep. 26, 2012

(86) PCT No.: PCT/KR2012/007774
§ 371 (c)(1),
(2) Date: May 21, 2014

(87) PCT Pub. No.: WO2010/048123
PCT Pub. Date: Apr. 4, 2013

(65) Prior Publication Data
US 2014/0309660 A1    Oct. 16, 2014

(30) Foreign Application Priority Data

Sep. 26, 2011    (KR) .................. 10-2011-0096947

(51) Int. Cl.
| | |
|---|---|
| *A61B 34/00* | (2016.01) |
| *A61B 19/00* | (2006.01) |
| *A61B 17/04* | (2006.01) |
| *A61B 34/30* | (2016.01) |
| *A61B 90/00* | (2016.01) |

(Continued)

(52) U.S. Cl.
CPC ...... *A61B 19/2203* (2013.01); *A61B 17/0469* (2013.01); *A61B 34/25* (2016.02); *A61B 34/30* (2016.02); *A61B 90/06* (2016.02); *A61B 5/0053* (2013.01); *A61B 5/14507* (2013.01); *A61B 5/14532* (2013.01); *A61B 5/14539* (2013.01); *A61B 5/14551* (2013.01); *A61B 5/4836* (2013.01); *A61B 17/0491* (2013.01); *A61B 17/06066* (2013.01); *A61B 17/06166* (2013.01); *A61B 34/10* (2016.02);

(Continued)

(58) Field of Classification Search
CPC ..... A61B 19/2203; A61B 34/25; A61B 34/30; A61B 90/06; A61B 17/0469; A61B 34/10; A61B 2034/108; A61B 2034/258; A61B 17/0491; A61B 17/06066
USPC ....................................................... 606/130
See application file for complete search history.

(56) References Cited

U.S. PATENT DOCUMENTS

| | | | | |
|---|---|---|---|---|
| 6,109,270 | A * | 8/2000 | Mah ............... | A61B 5/7264 |
| | | | | 128/924 |
| 2004/0243147 | A1* | 12/2004 | Lipow .............. | G09B 23/28 |
| | | | | 606/130 |
| 2012/0071863 | A1* | 3/2012 | Lee ................. | A61B 19/2203 |
| | | | | 606/1 |

FOREIGN PATENT DOCUMENTS

| | | |
|---|---|---|
| JP | 2004-254899 A | 9/2004 |
| JP | 2006-527445 A | 11/2006 |

(Continued)

*Primary Examiner* — Katrina Stransky
(74) *Attorney, Agent, or Firm* — Dinsmore & Shohl, LLP

(57) ABSTRACT

The present invention relates to an intelligent surgery system. According to one embodiment of the present invention, provided is an intelligent surgery system that comprises: a data-matching unit that receives, from an information-collecting apparatus, data on a part of the body of a patient that is to undergo surgery, and searches for control data matching the data on the part of the body to undergo surgery on the basis of a data-matching matrix; and a surgery control unit, which enables surgery tools or suturing devices to operate in accordance with the control data from the data-matching unit.

8 Claims, 3 Drawing Sheets

(51) Int. Cl.
  *A61B 17/06*    (2006.01)
  *A61B 17/00*    (2006.01)
  *A61B 5/00*     (2006.01)
  *A61B 5/145*    (2006.01)
  *A61B 5/1455*   (2006.01)
  *A61B 34/10*    (2016.01)

(52) U.S. Cl.
  CPC .............. *A61B 2017/00004* (2013.01); *A61B 2017/0496* (2013.01); *A61B 2034/108* (2016.02); *A61B 2034/258* (2016.02)

(56) References Cited

FOREIGN PATENT DOCUMENTS

| | | | |
|---|---|---|---|
| JP | 2007-080094 A | 3/2007 | |
| KR | 10-2009-0115162 A | 11/2009 | |
| KR | 10-2011-0004496 A | 1/2011 | |
| WO | WO 1998033451 * | 8/1998 | |
| WO | WO 2008104977 A2 * | 9/2008 | ........... A61B 5/0059 |

* cited by examiner

INTELLIGENT SURGERY SYSTEM

FIELD OF THE INVENTION

The present invention relates to an intelligent surgery system.

BACKGROUND

Surgical robots such as da Vinci™ or Amadeus™ have recently been in the spotlight, and active researches thereon are currently in progress. However, such conventional surgical robots still require complicated and skillful handling by surgeons, and have not been much concerned with accumulating and utilizing data on decisions made by individual surgeons when performing surgery.

Herein, the inventor(s) now present an intelligent surgery system to allow a user such as a surgeon to intelligently perform surgery, mainly in connection with suturing, which is one of the most common surgical procedures.

SUMMARY OF THE INVENTION

One object of the present invention is to provide a novel intelligent surgery system.

Another object of the invention is to collect and utilize data on a body area to undergo surgery so that automated or semi-automated surgery may be performed.

Yet another object of the invention is to utilize data matching so that surgery may be performed as standardized to a certain degree.

Still another object of the invention is to enable the contents of control data of a data matching matrix to be continuously improved in accordance with decisions of various users.

According to one aspect of the invention to achieve the objects as described above, there is provided an intelligent surgery system, comprising: a data matching unit to receive data on a surgical site of a patient from an information collection device and to find control data matching the data on the surgical site on the basis of a data matching matrix; and a surgery control unit to allow a surgical instrument or suturing device to operate in accordance with the control data from the data matching unit.

In addition, there may be further provided other configurations according to the technical idea of the invention.

According to the invention, there is provided a novel intelligent surgery system.

According to the invention, data on a body area to undergo surgery is utilized so that automated or semi-automated surgery may be performed.

According to the invention, data matching is utilized so that surgery may be performed as standardized to a certain degree.

According to the invention, the contents of control data of a data matching matrix may be continuously improved in accordance with decisions of various users.

DETAILED DESCRIPTION OF THE PREFERRED EMBODIMENTS

Figure 1:
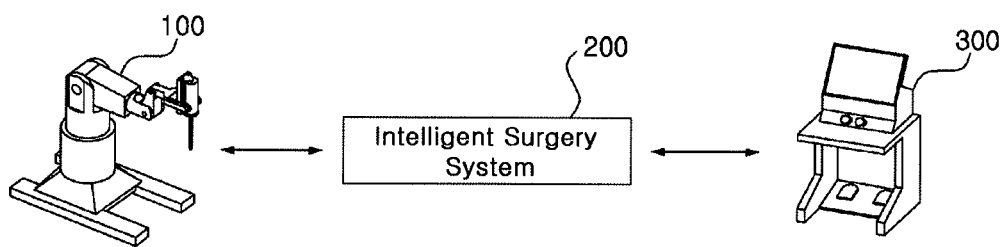
FIG. 1 shows the configuration of an overall system according to one embodiment of the invention.

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another embodiment without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of Overall System

Figure 2:
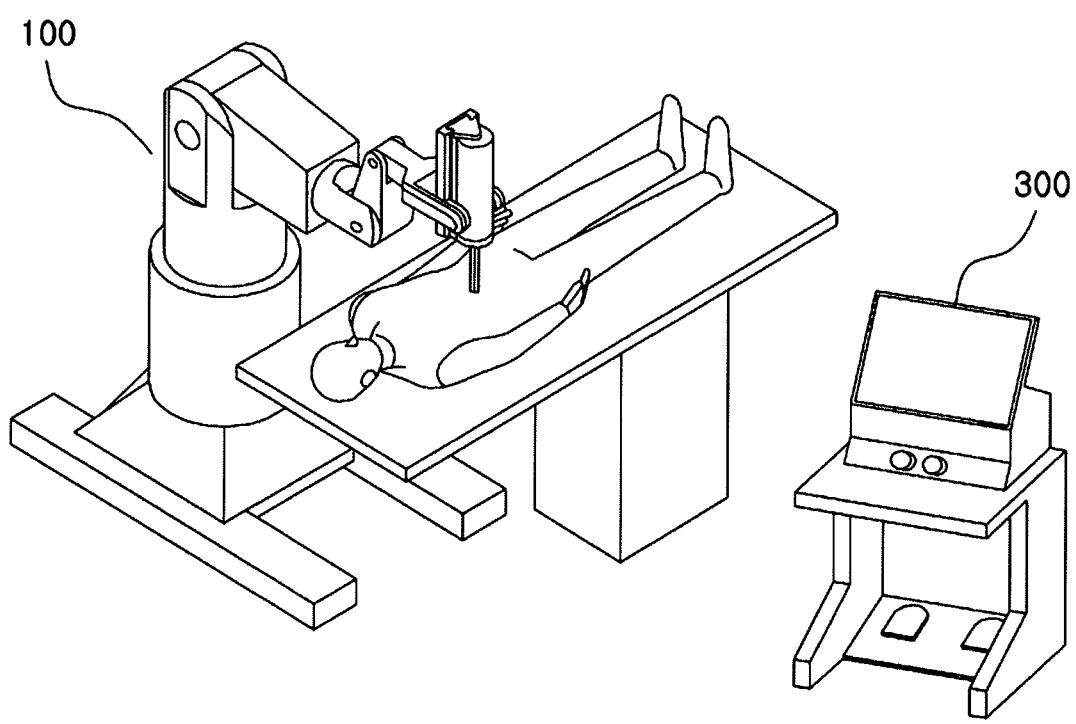
FIG. 2 shows a situation before a user actually performs surgery using the overall system.

FIG. 1 shows the configuration of an overall system according to one embodiment of the invention. As shown in FIG. 1, the overall system may be configured to comprise a robot 100 (more broadly, an automated medical device), an intelligent surgery system 200 and a user control device 300. Meanwhile, FIG. 2 shows a situation before a user actually performs surgery using the overall system.

First, the robot 100 according to one embodiment of the invention is a system comprising a base, a number of robotic arms, an endoscope, a surgical instrument (e.g., a clamp, a grasper, scissors, a stapler, a needle holder, or a set of at least some thereof), an information collection device, a suturing device and the like. This system may collect and provide data on a surgical site to the intelligent surgery system 200, and perform surgery by the control of the intelligent surgery system 200 or the user control device 300.

The information collection device that may be included in the robot 100 may comprise a probe similar to those disclosed in Korean Patent Application Nos. 1989-5618, 2005-33576 and the like, a sensor similar to those disclosed in Korean Patent Application Nos. 2004-51494, 2006-44711 and the like, or a measuring instrument similar to those disclosed in PCT International Application No. PCT/EP2006/011924 and the like (each of the disclosures of the above applications should be regarded as being incorporated herein by reference in its entirety). The information collection device may comprise at least one functional module configured with the above probe, sensor or measuring instrument, as necessary. Examples of the configurable functional modules are as follow:

(1) Elasticity Sensing Module

An elasticity sensing module may comprise a probe (which may be replaced with a general surgical needle), a probe driving unit and a data transmission unit. The probe driving unit is an element similar to that disclosed in PCT International Application No. PCT/KR2009/003419 (the disclosure of the above application should be regarded as being incorporated herein by reference in its entirety), and may move the probe to a surgical site (e.g. tissues) so that the probe may apply a predetermined pressure to the surgical site. In this case, the surgical site may be pressed and deformed by the probe, and the distance at which the probe moves during the deformation (e.g. for a predetermined time period) may be used to define the elasticity of the surgical site. Further, the data transmission unit is an element similar to those disclosed in Korean Patent Application Nos. 2004-51494, 2006-44711 and the like, and may calculate and transmit data on the elasticity of the surgical site to the intelligent surgery system 200.

(2) Temperature Sensing Module

A temperature sensing module may comprise a conventional thermometer for internal organs and a data transmission unit to transmit data on the temperature of the surgical site to the intelligent surgery system 200.

(3) Acidity Sensing Module

An acidity sensing module may comprise a conventional pH meter and a data transmission unit to transmit data on the acidity of the surgical site to the intelligent surgery system 200.

(4) Gas Pressure Sensing Module

There may be provided a gas pressure sensing module, which is as disclosed in Korean Patent Application Nos. 2004-51494, 2006-44711 and the like.

(5) Electromagnetic Property Sensing Module

There may be provided an electromagnetic property sensing module, which is as disclosed in Korean Patent Application No. 2005-33576 and the like (the disclosure of the above application should be regarded as being incorporated herein by reference in its entirety).

(6) Blood Property Detecting Module

A blood property detecting module may be a functional module to detect at least one of blood-related properties such as an oxygen saturation, a distribution of blood flow, a blood sugar level and the like. The blood property detecting module may comprise some components with functions similar to those of conventional oximeters or blood glucose meters. Further, the blood property detecting module may comprise a visual blood detecting component or a plurality of small blood detecting components to measure a distribution of blood flow in capillaries and the like in the surgical site. The plurality of small blood detecting components may preferably be disposed to contact a given surface together. When blood is detected at a relatively large number of the small blood detecting components, the distribution of the blood flow may be regarded as being dense, and vice versa. Further, the blood property detecting module may comprise a data transmission unit to transmit data on the blood properties of the surgical site to the intelligent surgery system 200.

(7) Body Fluid Property Detecting Module

As described above with the blood property detecting module, there may be provided a functional module to detect at least one property other than the blood properties, such as lymph fluid, intra-intestinal fluid (e.g. fluid in an oral cavity, esophagus, stomach, small intestine, large intestine or the like), intra-thoracic cavity fluid, intra-abdominal cavity fluid, urine component, feces component, pleural effusion and the like. The body fluid property detecting module may also be configured similarly to the blood property detecting module according to conventional techniques.

(8) Inflammation Detecting Module

An inflammation detecting module may be a functional module to detect an inflamed site or tissue necrosis. The inflammation detecting module may comprise some components with functions similar to those of conventional test kits, or may provide an extracted tissue to a conventional test kit disposed externally. Further, the inflammation detecting module may comprise a data transmission unit to transmit data on the test result to the intelligent surgery system 200.

(9) Other Modules

Referring to the configuration of the inflammation detecting module, there may be provided diverse modules capable of detecting cancer cells, specific proteins, minerals, fat layers or the like.

It will be apparent that the information collection device may comprise functional modules appropriately configured as necessary, so that data other than the above-exemplified data may also be collected and provided to the intelligent surgery system 200.

Meanwhile, the suturing device that may be included in the robot 100 may be implemented according to the techniques disclosed in PCT International Application Nos. PCT/KR2009/003419, PCT/KR2010/005851, PCT/KR2010/005852, PCT/KR2010/006448 and the like (each of the disclosures of the above applications should be regarded as being incorporated herein by reference in its entirety). In particular, the suturing device may adaptively select or adjust suturing modes, suture intervals, types of suture threads, or types of suture needles by the control of the intelligent surgery system 200. The adaptivity of the suturing device may also be implemented with reference to the above PCT international applications.

Meanwhile, among the surgical instrument or suturing device that may be included in the robot 100, the one to be actually used may be changed by the control of the intelligent surgery system 200 or the user control device 300.

The robot 100 may be configured without limitation by those skilled in the art, as long as it falls within the spirit of the present invention. In connection with the detailed configuration of the robot 100, reference may be made to Korean Patent Application No. 2008-108103 (the disclosure of the above application should be regarded as being incorporated herein by reference in its entirety).

Next, the intelligent surgery system 200 according to one embodiment of the invention may be a computer system to control the endoscope, surgical instrument, information collection device or suturing device of the robot 100, on the basis of the data from the information collection device of the robot 100 and, if necessary, information or commands that a user provides by means of the user control device 300, so that automated or semi-automated surgery may be performed. The detailed configuration of the intelligent surgery system 200 will be described later with reference to FIG. 3.

Lastly, the user control device 300 according to one embodiment of the invention may comprise display means, user input means, user command means and the like to enable a user to view a surgical site and the vicinity thereof, to input necessary information, to select and move the endoscope, surgical instrument, information collection device or suturing device, or to issue some commands to the above instruments or devices.

First, the display means of the user control device 300 may display to the user what is viewed by the endoscope (or a camera or the like) of the robot 100. To this end, the display means may comprise a display panel for two-dimensional display or a display space for three-dimensional display. Here, the display panel may be a known two-dimensional display device such as an LCD panel, a PDP panel and an LED display device which can display visual representations in two dimensions, and the display space may be a known three-dimensional display device such as a holographic display device.

Next, the user input means of the user control device 300 may allow the user to input information on a patient, e.g., basic information on race, age, sex and the like, condition information on blood pressure and the like, or information on the type of the surgical site. Various known computer input means such as a keyboard, mouse or touch screen may be employed as the user input means.

Lastly, the user command means of the user control device 300 may be various forms of command means to allow the user to issue a command for selecting or moving the endoscope, surgical instrument, information collection device or suturing device, or to command the surgical instrument or suturing device to perform surgical actions such as holding, fastening, searing, incising and suturing on the surgical site. The user command means may be implemented in the form of a control panel, control sticks, control buttons or the like separately from the display means, but may also be configured in combination with the display means. For example, if the display means is a touch panel, then the user command means may be the window or graphical buttons of the touch panel.

Configuration of Intelligent Surgery System

Figure 3:
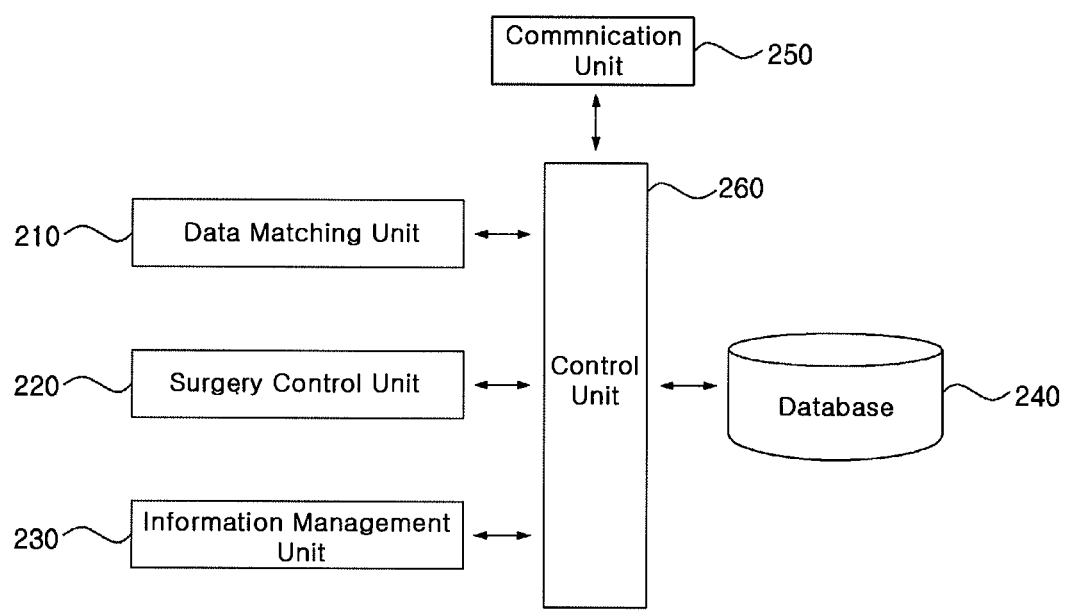
FIG. 3 shows in detail the internal configuration of an intelligent surgery system 200 according to one embodiment of the invention.

FIG. 3 shows in detail the internal configuration of the intelligent surgery system 200 according to one embodiment of the invention.

As shown in FIG. 3, the intelligent surgery system 200 according to one embodiment of the invention may be configured to comprise a data matching unit 210, a surgery control unit 220, a data management unit 230, a database 240, a communication unit 250 and a control unit 260. According to one embodiment of the invention, at least some of the data matching unit 210, the surgery control unit 220, the data management unit 230, the database 240, the communication unit 250 and the control unit 260 may be program modules to communicate with the robot 100 or the user control device 300. The program modules may be included in the intelligent surgery system 200 in the form of operating systems, application program modules or other program modules, while they may be physically stored in a variety of commonly known storage devices. Further, the program modules may also be stored in a remote storage device that may communicate with the intelligent surgery system 200. Meanwhile, such program modules may include, but not limited to, routines, subroutines, programs, objects, components, data structures and the like for performing specific tasks or executing specific abstract data types as will be described below in accordance with the present invention.

Meanwhile, the intelligent surgery system 200 may be configured to be physically separated from or combined with the robot 100 or the user control device 300, as desired by those skilled in the art.

First, the data matching unit 210 according to one embodiment of the invention may receive the aforementioned data from the information collection device of the robot 100, and, in some cases, receive the aforementioned information on the patient from the user control device 300. Further, the data matching unit 210 may find control data matching the received data or information with reference to a data matching matrix that may be stored in the database 240, and provide the control data to the surgery control unit 220.

As for the data matching matrix according to one embodiment of the invention, dimensions of the matrix may correspond to the types of the data from the information collection device and/or the types of the information on the patient from the user control device 300, categories of the dimensions of the matrix may correspond to the values or ranges of values of the data from the information collection device and/or the values or ranges of values of the information on the patient from the user control device 300, and elements of the matrix may correspond to the values of the control data on the surgical actions to be performed according to the corresponding data from the information collection device or the corresponding information from the user control device 300.

Examples of the data matching by the above data matching matrix are as follow:

1. The control data may be used to control the suture interval to be smaller as the age of the patient (except infants) is younger and the elasticity of the surgical site is higher or the distribution of the blood flow in the surgical site is denser.

2. When the internal temperature or the acidity of the surgical site is low, the control data may be used to increase the thickness of the suture thread or suture needle (e.g., for suturing of a stomach).

3. When a large amount of blood is detected at the surgical site, the control data may be used to change the suture thread to an insoluble suture thread capable of tolerating high pressure for a long period of time.

4. When the distribution of the blood flow in the surgical site becomes denser, the control data may be used to decrease the thickness of the suture thread or suture needle.

5. The control data may be used to decrease the suture interval or increase the tension of pulling the suture thread, when the surgical site is presumed to be arteries as red blood cells, white blood cells, a pressure of 120 mg and an oxygen saturation of more than 80% are detected or recognized therein.

6. On the contrary, the control data may be used to increase the suture interval or decrease the tension of pulling the suture thread when the surgical site is presumed to be veins.

7. The control data may be used to change the suture thread to a soluble thread for calculus prevention, when the surgical site has a tubular structure (the morphological information may be inputted by the user in advance) and urine component is detected at the surgical site.

8. The control data may be used to change the suture tread to an antibiotics-treated thread when the tissue necrosis is detected at the surgical site.

9. The control data may be used to change the suture thread to a suture thread easily identifiable by X-rays when cancer cells are detected at the surgical site.

10. The control data may be used to pause the suturing action of the suturing device or change the suturing mode when a large amount of blood, intestinal secretion, tissue necrosis or cancer cells are detected at the surgical site.

11. The control data may be used to stop the surgical instrument or suturing device when the elasticity of the surgical site is identified to be almost zero.

12. The control data may be used to change the surgical instrument to an electrocautery when a large amount of blood is detected at the surgical site.

13. The control data may be used to switch the mode of the electrocautery to a hemorrhage prevention mode when a large amount of blood is detected at the surgical site.

14. The control data may be used to change the surgical instrument to an electric knife, an electrocautery, a laser emitter or a drug spray when tissue necrosis or cancer cells are detected at the surgical site.

15. When the surgical instrument perform an action to hold the surgical site, the control data may be used to control the pressure of the action according to the elasticity of the surgical site.

Although only some of the examples of the possible data matching have been listed above, it will be apparent to those skilled in the art that more diverse examples of the data matching other than the above ones may be envisaged as accumulating and utilizing in combination the data from the information collection device or the information on the patient from the user control device 300.

Next, the surgery control unit 220 according to one embodiment of the invention may transmit to the robot 100 a control signal to allow the surgical instrument or suturing device to operate in accordance with the control data matched by the data matching unit 210. Further, the surgery control unit 220 may display to the user in advance the contents of the above operation control via the display means of the user control device 300.

The surgery control unit 220 may carry out automated control only depending on the matched control data, but may also carry out surgery control only after requesting and receiving the user's approval of the surgery control according to the matched control data. In the latter case, on the basis of the decision based on the user's surgical experience, the user may grant the above approval or else reject the approval and select the surgery control having the changed contents to be carried out.

Further, as the user issues a command by means of the user command device 300, the surgery control unit 220 may transmit to the robot 100 a control signal to control the operation of the base, robotic arms, endoscope, surgical instrument, information collection device, suturing device or the like.

Next, when the user makes a manipulation to change the contents of the surgery control using the user control device 300, the data management unit 230 according to one embodiment of the invention may significantly or slightly change the values or range of values of the corresponding matched control data (e.g., the control data on the suture interval, type of the suture thread, type of the suture needle, tension of pulling the suture thread, or the like) in accordance with the above contents, thereby updating the data matching matrix. In this case, the data management unit 230 may issue a message to the user to ask whether he/she wants the update, and request a confirmation from the user.

Next, the database 240 according to one embodiment of the invention may store the data matching matrix as described above. Although FIG. 3 shows that the database 240 is configured to belong to the intelligent surgery system 200, the database 240 may be configured separately from the intelligent surgery system 200, as needed by those skilled in the art to implement the invention. For example, the database 240 (and the data matching matrix thereof) may be built on a web server so that they may be consulted or updated by a large number of distributed users.

Next, the communication unit 250 according to one embodiment of the invention may perform a function to enable data transmission/receipt to/from the data matching unit 210, the surgery control unit 220, the data management unit 230 and the database 240.

Lastly, the control unit 260 according to one embodiment of the invention may perform a function to control data flow among the data matching unit 210, the surgery control unit 220, the data management unit 230, the database 240 and the communication unit 250. That is, the control unit 260 according to the present invention may control data flow into/out of the intelligent surgery system 200 or data flow among the respective components of the intelligent surgery system 200, such that the data matching unit 210, the surgery control unit 220, the data management unit 230, the database 240 and the communication unit 250 may carry out their particular functions, respectively.

The embodiments according to the present invention as described above may be implemented in the form of program instructions that can be executed by various computer components, and may be stored on a computer-readable recording medium. The computer-readable recording medium may include program instructions, data files, data structures and the like, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be changed to one or more software modules to perform the operations of the present invention, and vice versa.

Although the present invention has been described in terms of specific items such as detailed elements as well as the limited embodiments and the drawings, they are only provided to help general understanding of the invention, and the present invention is not limited to the above embodiments. It will be appreciated by a person of ordinary skill in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. An intelligent surgery system, comprising:
   a data matching unit configured to receive data on a surgical site of a patient from an information collection device;
   a database including a data matching matrix; and
   a surgery control unit,
   wherein dimensions of the data matching matrix correspond to the types of the data on the surgical site, categories of the dimensions correspond to values or ranges of values of the data on the surgical site, and elements of the data matching matrix correspond to values of control data;
   the data matching unit is configured to match the data on the surgical site with the data matching matrix, and retrieve one or more values of the values of the control data from the data matching matrix based on the matching; and
   the surgery control unit is configured to control a surgical instrument or suturing device based on the one or more of the values of control data.

2. An intelligent surgery system as claimed in claim 1, wherein the data on the surgical site is at least one of data on elasticity, temperature, acidity, gas pressure, electromagnetic property, blood property, body fluid property, inflammation and canceration of the surgical site.

3. An intelligent surgery system as claimed in claim 1, wherein the data matching unit further receives information on the patient provided by a user.

4. An intelligent surgery system as claimed in claim 3, wherein the information on the patient is information on at least one of race, age, sex and blood pressure of the patient, or information on the type of the surgical site.

5. An intelligent surgery system as claimed in claim 3, wherein the values of the control data are configured to control at least one of the type, mode and operating pressure of the surgical instrument.

6. An intelligent surgery system as claimed in claim 3, wherein the values of the control data are configured to control at least one of a suture interval, type of a suture thread, type of a suture needle, and tension of pulling the suture thread of the suturing device.

7. An intelligent surgery system as claimed in claim 1, wherein when a user makes a manipulation to change contents of surgery control, the values or range of values of the corresponding control data are capable of being updated in the data matching matrix.

8. An intelligent surgery system as claimed in claim 1, wherein the data matching matrix is capable of being updated on a web by a plurality of users.

\* \* \* \* \*